United States Patent [19]

Grisar et al.

[11] 4,367,236
[45] Jan. 4, 1983

[54] METHOD FOR THE TREATMENT OF CARDIAC FAILURE WITH ALKANOYLIMIDAZOL-2-ONE DERIVATIVES

[75] Inventors: J. Martin Grisar, Strasbourg, France; Richard A. Schnettler; Richard C. Dage, both of Cincinnati, Ohio

[73] Assignee: Merrell Dow Pharmaceuticals Inc., Cincinnati, Ohio

[21] Appl. No.: 317,962

[22] Filed: Nov. 4, 1981

[51] Int. Cl.$^3$ .................. A61K 31/415; A61K 31/44
[52] U.S. Cl. ................. 424/273 R; 424/263; 548/318; 548/321; 546/278
[58] Field of Search ................. 424/273 R, 263; 548/318, 321; 546/278

[56] References Cited

U.S. PATENT DOCUMENTS

| 2,441,933 | 5/1948 | Duschinsky | 548/321 |
| 2,441,935 | 5/1948 | Duschinsky | 548/321 |
| 2,514,380 | 7/1950 | Duschinsky | 548/321 |
| 3,303,199 | 2/1967 | Doebel et al. | 548/318 |
| 3,361,752 | 1/1968 | D'Amico | 548/321 |

FOREIGN PATENT DOCUMENTS 3021792  1/1981  Fed. Rep. of Germany .

OTHER PUBLICATIONS

Duschinsky et al., J. Am. Chem. Soc., 1948, vol. 70, pp. 657–662.
Dage et al., Fed. Proc., 1980, vol. 39, p. 1105 (Abstract).
Kondo et al., J. Org. Chem., 1979, vol. 44 (24), pp. 4430–4435.
Duschinsky et al., J. Am. Chem. Soc., 1946, vol. 68, pp. 2350–2355.

*Primary Examiner*—Henry R. Jiles
*Assistant Examiner*—Natalia Harkaway
*Attorney, Agent, or Firm*—Stephen L. Nesbitt; Raymond A. McDonald; Gary D. Street

[57] ABSTRACT

4-Alkanoylimidazol-2-ones of the following general structure which are useful as cardiotonics in the treatment of cardiac failure wherein Q and T are each an oxygen atom or a divalent sulfur atom; R is hydrogen, lower alkyl, lower alkylcarbonyl or benzoyl; $R_1$ is hydrogen or lower alkyl; $R_2$ is a lower aliphatic hydrocarbon radical, phenyl alkylene or heterocyclo alkylene; and the pharmaceutically acceptable salts thereof.

8 Claims, No Drawings

METHOD FOR THE TREATMENT OF CARDIAC FAILURE WITH ALKANOYLIMIDAZOL-2-ONE DERIVATIVES

FIELD OF THE INVENTION

This invention relates to substituted alkanoylimidazol-2-ones and their use as cardiotonics in the treatment of cardiac failure.

SUMMARY OF THE INVENTION

This invention is directed to pharmaceutically active substituted alkanoylimidazol-2-ones of the general Formula 1

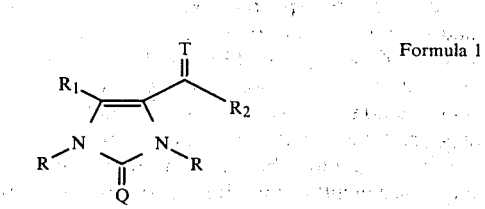

Formula 1 wherein Q and T are each an oxygen atom or a divalent sulfur atom; R is hydrogen, lower alkyl, lower alkanoyl or benzoyl; $R_1$ is hydrogen or lower alkyl; $R_2$ is a lower aliphatic hydrocarbon radical, phenyl alkylene, or heterocycloalkylene; and the pharmaceutically acceptable salts thereof. These compounds are useful as cardiotonics in the treatment of cardiac failure.

DESCRIPTION OF THE PREFERRED EMBODIMENTS

As used herein, the term "lower alkyl" includes straight and branched chain alkyl groups of from 1 to 4 carbon atoms such as methyl, ethyl, n-propyl, isopropyl, n-butyl and isobutyl. The term "lower alkanoyl" includes straight and branched chain alkanoyl groups of from 1 to 4 carbon atoms such as acetyl, propionyl, n-butyryl or isobutyryl. The term "lower alkylthio" includes straight and branched chain alkylthio of from 1 to 4 carbon atoms. The term "alkylene" includes the straight and branched chain alkylene radicals having from 1 to 6 carbon atoms which can be olefinically or acetylinically unsaturated with 1 or 2 double or triple bonds. Illustrative of the alkylene groups of this invention are methylene, ethylene, propylene, 1,3-butadienediylidene, butadiynylene, 2-butenylene, 2,4-hexadiynylene, hexamethylene, ethenylidene and isopropylidene.

The term "lower aliphatic hydrocarbon radical" includes saturated straight or branched chain alkyl groups of from 2 to 8 carbon atoms, cycloalkyl or cycloalkenyl of from 3 to 7 carbon atoms and cycloalkylalkylene or cycloalkenylalkylene wherein the cycloalkyl or cycloalkenyl moiety has from 3 to 7 carbon atoms. Illustrative of the lower aliphatic hydrocarbon radicals of this invention are ethyl, isopropyl, sec-butyl, octyl, 1,1-dimethylpropyl, cyclopropyl, cyclobutene, cyclohexene, cycloheptane, 2-butanyl, 2-methylpropylidene and 4-methylpentyl.

As used herein, the term "phenyl" is taken to mean a group of the formula

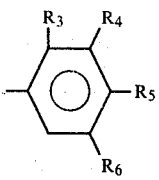

wherein $R_3$ is hydrogen, lower alkyl, lower alkoxy or lower alkylthio; $R_4$, $R_5$ and $R_6$ are each hydrogen, lower alkyl, lower alkoxy or lower alkylthio; and adjacent $R_3$, $R_4$, $R_5$ and $R_6$ groups taken together can be a methylenedioxy group optionally substituted with one or two methyl groups. Illustrative examples of phenylalkylene as used herein are 2-(3-methoxyphenyl)ethylene and benzyl.

As used herein, the term "heterocyclo" includes furanylalkylene, thienylalkylene, pyridylalkylene, and pyrrylalkylene. Furanyl includes 2-furanyl and 3-furanyl. Thienyl includes 2-thienyl and 3-thienyl. Pyridyl includes 2-pyridyl, 3-pyridyl and 4-pyridyl. Pyrryl includes 2-(1H-pyrryl) and 3-(1H-pyrryl). Illustrative examples of heterocyclo alkylene groups as used herein are 3-(2-thienyl)propylene, 4-(2-pyridyl)-2-butenylene and 3-furanylmethylene.

The preferred compounds of this invention are those compounds of Formula I wherein Q and T are both oxygen atoms and R is hydrogen.

The more preferred compounds of this invention are those compounds of Formula 1 wherein $R_2$ is a straight or branched chain saturated alkyl group of from 2 to 8 carbon atoms or $R_2$ is phenylalkylene and wherein $R_1$ is hydrogen, methyl and ethyl.

The most preferred compounds of this invention are those compounds of Formula 1 wherein $R_2$ is ethyl, isopropyl or cyclopropyl and wherein $R_1$ is methyl or ethyl.

As examples of compounds of Formula 1 there may be mentioned the following:

4-cyclopropylcarbonyl-1,3-dihydro-5-methyl-2H-imidazol-2-one;

1,3-dihydro-4-isobutyryl-2H-imidazol-2-thione;

1,3-dihydro-4-ethyl-5-thiopropionyl-2H-imidazol-2-one;

1,3-dihydro-1,3-dimethyl-4-ethyl-5-propionyl-2H-imidazol-2-one;

1,3-dihydro-4-methyl-5-(2-phenylacetyl)-2H-imidazol-2-one;

1,3diacetyl-1,3-dihydro-4-[3-(4-methylphenyl)-1-onepropyl]-2H-imidazol-2-one;

1,3-dihydro-4-[2-[(2,4-dimethylthio)phenyl]acetyl]-2H-imidazol-2-one;

1,3-dihydro-4-ethyl-5-[3-(3,4-methylenedioxyphenyl)-2-methyl-1-oxopropyl]-2H-imidazol-2-one;

4-(n-butyl)-1,3-dihydro-5-[2-(3,5-diethoxyphenyl)acetyl]-2H-imidazol-2-one;

1,3-dibenzoyl-1,3-dihydro-4-[2-(2-furyl)acetyl]-2H-imidazol-2-one;

1,3-dihydro-4-isopropyl-5-[4-(3-thienyl)-1-oxobutyl]-2H-imidazol-2-one;

1,3-dihydro-4-methyl-5-(1-oxopropyl)-2H-imidazol-2-one;

1,3-dihydro-4-butyryl-2H-imidazol-2-one;

1,3-dihydro-4-methyl-5-propionyl-2H-imidazol-2-thione;

1,3-dihydro-4-[2-[4-(methylthio)phenylacetyl]]-5-propyl-2H-imidazol-2-one;

1,3-dihydro-4-methyl-5-[2-phenyl(thioacetyl)]-2H-imidazol-2-thione; and 4-cinnamoyl-1,3-dihydro-5-isopropyl-2H-imidazol-2-one.

Those compounds of Formula I wherein R is hydrogen, are acidic and may form pharmaceutically active salts of Formula 2

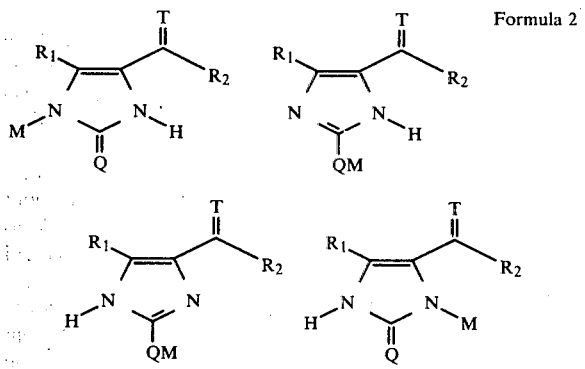

Formula 2 wherein Q, T, $R_1$ and $R_2$ are as defined in Formula 1, and M is a pharmaceutically acceptable alkali metal such as sodium or potassium; alkaline earth metal such as calcium or magnesium; transition metal such as zinc or iron; main group metal; ammonium or organic ammonium ion such as tetramethylammonium ion.

In general, the compounds of this invention are prepared by standard techniques analogously known in the art.

More specifically, the substituted alkanoylimidazol-2-ones of this invention wherein Q and T are each an oxygen atom and R is hydrogen may be prepared by a Friedel-Crafts acylation of an imidazol-2-one of Formula 3

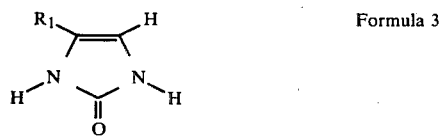

Formula 3 wherein $R_1$ is as defined in Formula 1. The acylating agent used in the Friedel-Crafts reaction can be an alkanoyl halide of Formula 4

Formula 4 wherein $R_2$ is as defined in Formula 1 and X is a halogen atom such as bromine, iodine or preferably chlorine. Furthermore, the Friedel-Crafts reaction may be performed on the free acid or its corresponding acid anhydride instead of the alkanoyl halides mentioned hereinabove employing essentially identical reaction conditions. These alternate reactions are more fully described in Olah, "Friedel-Crafts and Related Reactions," Vol. III, Part 1, Interscience Publications, John Wiley and Sons, New York, 1964.

The Friedel-Crafts reactions of this invention are performed by premixing about 1 molar equivalent of the appropriate imidazol-2-one with about 1 molar equivalent to about 10 molar equivalents, preferably about 2 molar equivalents, of a Lewis acid catalyst in a suitable solvent, for example, petroleum ethers; a chlorinated hydrocarbon, such as carbon tetrachloride, ethylene chloride, dichloromethane or chloroform; a chlorinated aromatic, such as 1,2,4-trichlorobenzene or o-dichlorobenzene; carbon disulfide; or nitrobenzene. The preferred solvent is dichloromethane. About 1 molar equivalent to about 10 molar equivalents, preferably about 1.1 molar equivalents of the appropriate alkanoyl halide of Formula 4 is added, preferably dropwise, to the mixture of imidazol-2-one, Lewis acid, and solvent and the reaction is allowed to proceed for about ½ hour to about 100 hours, preferably from about 1 hour to about 10 hours depending on the reactants, the solvent, and the temperature which can be from about $-78°$ to about 150° C., preferably about 0° to about 100° C., most preferably about 60° C. The resulting alkanoylimidazol-2-one may be isolated from the reaction mixture by any suitable art-known procedure, preferably by quenching the reaction mixture with ice water and subsequently removing the product by filtration or extraction.

Lewis acid catalysts suitable for use in the Friedel-Crafts reactions described herein are, for example, a metal, such as aluminum, cerium, copper, iron, molybdenum, tungsten or zinc; a Bronstead acid, such as a phosphoric acid, sulfuric acid, sulfonic acid, or a hydrohalo acid, such as hydrochloric or hydrobromic acid; halogen substituted acetic acids, such as chloroacetic or trifluoroacetic acids; or a metallic halide, such as a boron halide, zinc chloride, zinc bromide, berryl chloride, copper chloride, iron(III) bromide, iron(III) chloride, mercury(II) chloride, mercury(I) chloride, antimony bromide, antimony chloride, titanium(IV) bromide, titanium(IV) chloride, titanium(III) chloride, aluminum bromide or preferably aluminum chloride.

The substituted alkanoylimidazol-2-ones of this invention wherein T is an oxygen atom and R is hydrogen may be prepared by reaction of an aminodiketone of Formula 5

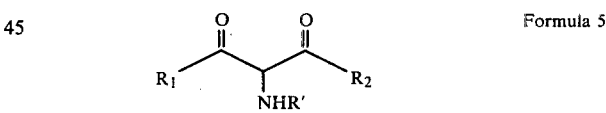

Formula 5 wherein $R_1$ and $R_2$ are as defined in Formula 1 and R' is hydrogen or a lower alkylcarbonyl, preferably methylcarbonyl(acetyl) with a cyanate or thiocyanate salt, as appropriate, preferably sodium or potassium cyanate or thiocyanate. This reaction is performed by mixing about 1 molar equivalent of the appropriate aminodiketone with about 1 to about 5 molar equivalents, preferably about 1 molar equivalent of a cyanate or thiocyanate salt in a suitable solvent. The reaction is allowed to proceed for about 5 minutes to about 1 hour depending on the reactants, the solvent and the temperature which can be from about $-10°$ to about 50° C., preferably 0° C. Suitable solvents for this reaction are any non-reactive solvents, preferably water or a water soluble solvent, for example, an organic acid such as acetic acid; an alcohol such as methanol or ethanol; or an ether such as tetrahydrofuran or p-dioxan. Preferably a nonaqueous solvent is mixed with water. The preferred solvent is aqueous ethanol.

The product of this reaction may be isolated by any art-known procedure such as by conversion to the corresponding sodium or potassium salt and reprecipitation with carbon dioxide or a mineral acid such as dilute hydrochloric acid.

When it is desired that T be a divalent sulfur atom, the corresponding alkanoylimidazol-2-one of Formula 1 wherein T is an oxygen atom is reacted with phosphorus pentasulfide, $P_2S_5$, by procedures generally known in the art. This reaction may be performed by mixing about 1 molar equivalent of the alkanoylimidazol-2-one of Formula 1 wherein T is an oxygen atom with about 1 to about 5 molar equivalents, preferably about 1 molar equivalent, of $P_2S_5$, together with a suitable solvent. This reaction is allowed to proceed for about 1 to about 10 hours, preferably about 5 hours, depending on the reactant, the solvent and the temperature which can be from about 25° C. to about 125° C., preferably about 80° C. A suitable solvent for this reaction is any non-reactive solvent, for example, a petroleum ether; a chlorinated hydrocarbon such as chloroform, methylene chloride, carbon tetrachloride or ethylene chloride; an etheral solvent such as diethyl ether, tetrahydrofuran or p-dioxan; an aromatic solvent such as benzene, toluene or xylene; or pyridine. The preferred solvent is pyridine.

When desired, one or both of the nitrogen atoms of the alkanoylimidazol-2-one ring may be substituted with an alkyl group by any art-known procedure. Such methods include reacting the appropriate N-unsubstituted alkanoylimidazol-2-one of Formula 1 wherein R is hydrogen, with a base and an alkylating agent in presence of an unreactive solvent. Suitable bases for this reaction can be, for example, a hydride such as sodium hydride or calcium hydride; a phenoxide such as sodium phenoxide; an alkoxide such as sodium ethoxide; or preferably a hydroxide such as sodium hydroxide. Suitable alkylating agents for this reaction are, for example, an alkyl halide such as methyl iodide; or a dialkylsulfate such as dimethylsulfate. Suitable unreactive solvents are, for example, dimethylformamide (DMF) or dimethylsulfoxide (DMSO). The reaction is allowed to proceed from about 1 minute to about 1 hour and the temperature may be from about 0° C. to about 100° C., preferably about 25° C. When it is desired that only one of the alkanoylimidazol-2-one nitrogen atoms be substituted with an alkyl group, the appropriate alkanoylimidazol-2-one is reacted with from about 1 molar equivalent to about 10 molar equivalents of a base, preferably about 1 molar equivalent and with about 1 molar equivalent of an alkylating agent. Utilizing this procedure, both possible monoalkylated nitrogen isomers result. These isomers are separable by conventional art-known procedures such as fractional crystallization, fractional distillation, or chromatography. When it is desired that both nitrogen atoms of the alkanoylimidazol-2-one ring be alkyl substituted, the appropriate alkanoylimidazol-2-one is reacted with from about 2 molar equivalents to about 10 molar equivalents of a base, preferably about 2 molar equivalents and from about 2 molar equivalents to about 10 molar equivalents of an alkylating agent, preferably about 2 molar equivalents.

When desired, the nitrogen atoms of the alkanoylimidazol-2-one ring may be substituted with an alkanoyl or benzoyl group by any suitable art-known procedure. Such methods include reacting the ring N-unsubstituted alkanoylimidazol-2-one of Formula 1 wherein R is hydrogen with an alkanoyl or benzoyl halide, preferably an alkanoyl or benzoyl halide, preferably an alkanoyl or benzoyl chloride such as acetyl chloride, n-propanoyl chloride, isopropanoyl chloride or butanoyl chloride. Normally, acylation reactions utilizing alkanoyl or benzoyl halides employ an acid sponge such as triethylamine or pyridine to remove any hydrohalide as it is formed. Furthermore, the corresponding free acid or acid anhydride may be employed instead of the acyl or benzoyl halides. Acylation and benzoylation reactions are generally run without added solvent but may be performed using any nonreactive solvent, for example, petroleum ethers; chlorinated hydrocarbons such as chloroform, methylene chloride or carbon tetrachloride; carbon disulfide; ethereal solvents such as diethylether, tetrahydrofuran or p-dioxan; or aromatic solvents such as benzene, toluene or xylene. The reactions are allowed to proceed for about 1 minute to about 100 hours, preferably from about 1 hour to about 10 hours and the temperature may be from about −78° to about 150° C., preferably from 0° to 100° C.

The alkali metal, alkaline earth metal, transition metal, main group metal salts of the alkanoylimidazol-2-ones of this invention may be prepared from a corresponding metal salt for example an alkoxide, such as sodium methoxide or sodium ethoxide; a phenoxide, such as sodium phenoxide; hydroxides, such as sodium hydroxide or potassium hydroxide. These reactions may be performed with or without a solvent. Suitable solvents are, for example, lower alcohols, such as methanol, ethanol, isopropanol, n-propanol or n-butanol; dimethylformamide (DMF); or dimethylsulfoxide (DMSO). The solvents may be used with or without added water.

The alkanoylimidazol-2-one and base are allowed to react for about 1 minute to about 24 hours depending on the reactants and the temperature which can be from about −78° to about 150° C., preferably about 0° to about 25° C.

The aminodiketones of Formula 5 may be prepared by reduction of the appropriate oxime of Formula 6

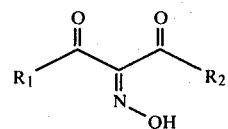

Formula 6 wherein $R_1$ and $R_2$ are as defined above in Formula 1. These oximes are reduced by any suitable method generally known in the art such as catalytically in acidic alcoholic medium such as ethanol over an appropriate noble metal catalyst such as palladium on charcoal or with zinc or tin in acetic acid/acetic anhydride solution.

The oximes of Formula 6 may be prepared by any suitable art-known procedure such as nitrosation of the appropriate diketone of Formula 7

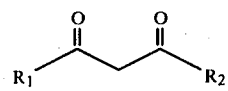

Formula 7 wherein $R_1$ and $R_2$ are as defined above in Formula 1. Suitable nitrosation reactions are reviewed by O. Tousler in "Organic Reactions," volume VII, pp. 327-377.

The compounds of general Formula 1 may be used in the treatment of cardiac failure including congestive heart failure, backward heart failure, forward heart failure, left ventricular heart failure, or right ventricular heart failure or in the treatment of any other condition which requires the strengthening of heart action with a cardiotonic. In many respects these compounds possess digitalis-like action but possess much less toxicity. When administered, the compounds of Formula 1 increase cardiac contractile force, while heart rate is increased to a significantly lesser degree. In patients suffering from "heart failure" administration of the compounds of Formula 1 increased cardiac output and stroke volume while decreasing left atrial pressure indicating marked improvement in pump function of the heart.

The utility of Formula 1 compounds as cardiotonics may be determined by administering the test compound (0.1–10 mg/kg) intravenously, intraperitoneally, intraduodenally or intragastrically in a suitable vehicle to a mongrel dog (either sex). The test dogs are anesthetized and prepared by isolating a suitable artery (e.g., femoral or common carotid) and vein (e.g., femoral or external jugular); introducing polyethylene catheters filled with 0.1% Heparin-Na to record arterial blood pressure and administer compounds, respectively. The chest is opened by splitting the sternum at the midline or by an incision at the left fifth intercostal space. A Brodie-Walton strain gage is sutured to the right or left ventricle to monitor myocardial contractile force. An electromagnetic flow probe may be placed around the root of the ascending aorta for measuring cardiac output less coronary blood flow. Heart failure is induced by administering sodium pentobarbitol (20–40 mg/kg) or propranalol hydrochloride (3–5 mg/kg) to the blood perfusing the heart. Following administration of either of these cardiac depressants, the right atrial pressure dramatically increases and cardiac output is severely depressed. Reversal of these effects by the test compound indicates cardiotonic activity.

The compounds may be administered in various manners to achieve the desired effect. The compounds may be administered alone or in the form of pharmaceutical preparations to the patient being treated either orally or parenterally, that is, intravenously or intramuscularly. The amount of compound administered will vary with the severity of cardiac failure and the mode of administration.

For oral or parenteral administration the cardiotonically effective amount of compound is from about 0.1 mg/kg of patient body weight per day up to about 500 mg/kg of patient body weight per day and preferably from about 0.1 mg/kg of patient body weight per day up to about 100 mg/kg of patient body weight per day.

For oral administration a unit dosage may contain, for example, from 5 to 500 mg of the active ingredient. For parenteral administration a unit dosage may contain, for example, from 5 to 50 mg of the active ingredient. Repetitive daily administration of the compounds may be desired and will vary with the condition of the patient and the mode of administration.

As used herein, the term patient is taken to mean a warm blooded animal, for example, birds, such as chickens and turkeys, and mammals, such as primates, humans, sheep, horses, bovine cows and bulls, pigs, dogs, cats, rats and mice.

For oral administration the compounds can be formulated into solid or liquid preparations such as capsules, pills, tablets, troches, powders, solutions, suspensions, or emulsions. The solid unit dosage forms can be a capsule which can be of the ordinary gelatin type containing, for example, lubricants and inert filler, such as lactose, sucrose and cornstarch. In another embodiment the compounds of general Formula 1 can be tableted with conventional tablet bases such as lactose, sucrose and cornstarch in combination with binders, such as acacia, cornstarch or gelatin, disintegrating agents such as potato starch or alginic acid, and a lubricant such as stearic acid or magnesium stearate.

For parenteral administration the compounds may be administered as injectable dosages of a solution or suspension of the compound in a physiologically acceptable diluent with a pharmaceutical carrier which can be a sterile liquid such as water and oils with or without the addition of a surfactant and other pharmaceutically acceptable adjuvants. Illustrative of oils which can be employed in these preparations are those of petroleum, animal, vegetable, or synthetic origin, for example, peanut oil, soybean oil and mineral oil. In general, water, saline, aqueous dextrose and related sugar solutions, ethanol and glycols such as propylene glycol or polyethylene glycol are preferred liquid carriers, particularly for injectable solutions.

The compounds can be administered in the form of a depot injection or implant preparation which may be formulated in such a manner as to permit a sustained release of the active ingredient. The active ingredient can be compressed into pellets or small cylinders and implanted subcutaneously or intramuscularly as depot injections or implants. Implants may employ inert materials such as biodegradable polymers or synthetic silicones, for example, Silastic, silicone rubber manufactured by the Dow-Corning Corporation.

The following are illustrative examples of the preparation and use of the compounds of this invention.

EXAMPLE 1

1,3-Dihydro-4-methyl-5-(1-oxopropyl)-2$\underline{H}$-imidazol-2-one

To 13.3 g (0.1 mole) of aluminum chloride under 150 ml of dry dichloromethane is added 4.9 g (0.05 mole) of 1,3-dihydro-4-methyl-2$\underline{H}$-imidazol-2-one and, dropwise, 5.1 g (0.055 mole) of propionyl chloride. The mixture is stirred and heated to reflux temperature for 6 hours. The mixture is cooled and 2 N hydrochloric acid (150 ml) is added dropwise. The resulting precipitate is collected, washed with water and dichloromethane and recrystallized from 50% aqueous ethanol to give the title compound, m.p. 270°–271° C.

Substituting valeroyl chloride for propionyl chloride gives 1,3-dihydro-4-methyl-5-(1-oxopentyl)-2$\underline{H}$-imidazol-2-one, m.p. 222°–224° C.

Substituting octanoyl chloride for propionyl chloride gives 1,3-dihydro-4-methyl-5-(1-oxooctyl)-2$\underline{H}$-imidazol-2-one, m.p. 220°–221° C.

Substituting tert-butylacetyl chloride for propionyl chloride gives 1,3-dihydro-4-methyl-5-(1-oxo-3-dimethylbutyl)-2$\underline{H}$-imidazol-2-one, m.p. 261°–262° C.

Substituting isovaleroyl chloride for propionyl chloride gives 1,3-dihydro-4-methyl-5-(1-oxo-3-methylbutyl)-2$\underline{H}$-imidazol-2-one, m.p. 232°–233° C.

EXAMPLE 2

1,3-Dihydro-4-ethyl-5-(1-oxo-2-methylpropyl)-2H-imidazol-2-one

To 13.3 g (0.1 mole) of aluminum chloride under 150 ml of dry dichloromethane is added 5.8 g (0.05 mole) of 1,2-dihydro-4-ethyl-2H-imidazol-2-one and, dropwise, 5.9 g (0.055 mole) of isobutyryl chloride. The mixture is stirred and heated to reflux for 4 hours. The mixture is cooled and 2 N hydrochloric acid (150 ml) is added dropwise. The resulting precipitate is collected, washed with water and dichloromethane and recrystallized from ethanol containing 10–30% of water to give the title compound. M.p. 206°–208° C.

Substituting propanoyl chloride for isobutyryl chloride gives 1,3-dihydro-4-ethyl-5-(1-oxopropyl)-2H-imidazol-2-one, m.p. 212°–213° C.

Substituting 2-ethylbutyryl chloride for isobutyryl chloride gives 1,3-dihydro-4-ethyl-5-(1-oxo-2-ethylbutyl)-2H-imidazol-2-one.

EXAMPLE 3

1,3-Dihydro-4-(1-oxobutyl)-2H-imidazol-2-one

In 10 ml of dichloromethane is placed 1.0 g of 1,3-dihydro-2H-imidazol-2-one, 1.28 g of butyryl chloride and 4.8 g of aluminum chloride. The mixture is refluxed and stirred for 2 hours after which it is poured into water. The precipitate is collected, washed with water, and recrystallized from ethanol:water, to give the title compound, m.p. 268°–270° C.

Substituting hexanoyl chloride for butyryl chloride gives 1,3-dihydro-4-(1-oxohexyl)-2H-imidazol-2-one.

Substituting 2-ethylhexanoyl chloride for butyryl chloride gives 1,3-dihydro-4-(1-oxo-2-ethylhexyl)-2H-imidazol-2-one.

EXAMPLE 4

1,3-Dihydro-4-methyl-5-(1-cyclopropyl-1-oxomethyl)-2H-imidazol-2-one

To 13.3 g of aluminum chloride under 200 ml of dry methylene chloride is added 4.9 g of 1,2-dihydro-4-methyl-2H-imidazol-2-one and, dropwise, 5.7 g of cyclopropanecarboxylic acid chloride. The mixture is stirred and heated to reflux for 5 hours. The mixture is cooled and 2 N hydrochloric acid (150 ml) is added dropwise. The resulting precipitate is collected, washed with water and methylene chloride and recrystallized twice from ethanol-water (4:1) gives the title compound. m.p. 272°–273° C.

Substituting cyclopropanecarboxylic acid chloride with cyclobutanecarboxylic acid chloride or cyclohexanecarboxylic acid chloride gives 1,3-dihydro-4-methyl-5-(1-cyclobutyl-1-oxomethyl)-2H-imidazol-2-one, and 1,3-dihydro-4-methyl-5-(1-cyclohexyl-1-oxomethyl)-2H-imidazol-2-one, m.p. 279°–281° C. and 280°–282° C., respectively.

Substituting 1-cyclopentenecarboxylic acid chloride for cyclopropanecarboxylic acid chloride gives 1,3-dihydro-4-methyl-5-[1-(1-cyclopentenyl)-1-oxomethyl]-2H-imidazol-2-one.

EXAMPLE 5

1,3-Dihydro-4-methyl-5-(2-phenylacetyl)-2H-imidazol-2-one

To 26.6 g (0.2 mole) of aluminum chloride in 250 ml of dichloromethane is added 9.8 g (0.1 mole) of 1,3-dihydro-4-methyl-2H-imidazol-2-one and, dropwise, 16.9 g (0.11 mole) of phenylacetyl chloride. The mixture is stirred and heated to reflux for 5 hours. The mixture is cooled and 200 ml of 2 N-hydrochloric acid is added dropwise. The resulting precipitate is collected, washed with water, and recrystallized from 50% aqueous ethanol to give the title compound, m.p. 239°–240° C.

Substituting 3-phenylbutyric acid chloride for phenylacetyl chloride gives 1,3-dihydro-4-methyl-5-(1-oxo-3-phenylbutyl)-2H-imidazol-2-one.

Substituting p-chlorophenylacetyl chloride for phenylacetyl chloride gives 1,3-dihydro-5-[2-(4-chlorophenyl)acetyl]-4-methyl-2H-imidazol-2-one.

Substituting 3-(o-methoxyphenyl)propionyl chloride for phenylacetyl chloride gives 1,3-dihydro-4-methyl-5-[1-oxo-3-(2-methoxyphenyl)propyl]-2H-imidazol-2-one.

Substituting 2-(4-thiomethylphenyl)acetyl chloride for phenylacetyl chloride gives 1,3-dihydro-4-methyl-5-[2-(4-thiomethylphenyl)acetyl]-2H-imidazol-2-one.

Substituting 2-pyridylacetyl chloride for phenylacetyl chloride gives 1,3-dihydro-4-methyl-5-[2-(2-pyridinyl)acetyl]-2H-imidazol-2-one.

Substituting 5-methyl-2-pyrrolepropanoic acid chloride for phenylacetyl chloride gives 1,3-dihydro-4-methyl-5-[1-oxo-3-(5-methyl-1H-pyrrol-2-yl)propyl]-2H-imidazol-2-one.

Substituting 3-thiopheneacetic acid chloride for phenylacetyl chloride gives 1,3-dihydro-4-methyl-5-[2-(3-thienyl)acetyl]-2H-imidazol-2-one.

Substituting 2-cyclopentene-1-acetic acid chloride for phenylacetyl chloride gives 1,3-dihydro-4-methyl-5-[1-oxo-2-(2-cyclopentenyl)ethyl]-2H-imidazol-2-one.

EXAMPLE 6

1,3-Dihydro-4-methyl-5-(1-oxo-3-phenyl-2-propenyl)-2H-imidazol-2-one

To 3.3 g of aluminum chloride under 50 ml of nitrobenzene is added 4.9 g of 1,2-dihydro-4-methyl-2H-imidazol-2-one and 8.3 g of cinnamoyl chloride. The mixture is stirred and heated on a steam bath for 1 hour and then poured on ice. The resulting precipitate is collected, washed with water and recrystallized twice from methanol and dimethylsulfoxide-water, respectively, to give the title compound, m.p. 299° C.

Substituting cinnamoyl chloride by styrylacetic acid chloride gives 1,3-dihydro-4-methyl-5-(1-oxo-4-phenyl-3-butenyl)-2H-imidazol-2-one.

Substituting cinnamoyl chloride by β-(3-pyridyl)acrylic acid chloride gives 1,3-dihydro-4-methyl-5-[1-oxo-3-(3-pyridinyl)-2-propenyl]-2H-imidazol-2-one.

Substituting cinnamoyl chloride by 2-thiopheneacrylic acid chloride gives 1,3-dihydro-4-methyl-5-[1-oxo-3-(2-thienyl)-2-propenyl]-2H-imidazol-2-one.

EXAMPLE 7

1,3-Dihydro-4-methyl-5-(1-oxopropyl)-2H-imidazol-2-thione

Ten grams of 3-amino-2,4-hexanedione hydrochloride are dissolved in 100 ml water. Fifteen grams of potassium thiocyanate are added and the mixture is heated on the steam bath for 10 minutes. On cooling, the title compound is obtained.

In like manner, substituting 3-amino-6-phenyl-2,4-hexanedione hydrochloride, 3-amino-5-(2-furanyl)-2,4-pentanedione hydrochloride, or 4-amino-2-(2-pyridyl)-3,5-heptanedione hydrochloride for 3-amino-2,4-hexanedione hydrochloride in the above example yields, respectively, 1,3-dihydro-4-methyl-5-(3-phenyl-1-oxopropyl)-2H-imidazol-2-thione, 1,3-dihydro-4-(2-furanyl)acetyl-5-methyl-2H-imidazol-2-thione, or 1,3-dihydro-4-ethyl-5-[2-(2-pyridyl)-1-oxopropyl]-2H-imidazol-2-thione.

EXAMPLE 8

1,3-Dihydro-4-methyl-5-(1-thioxo-2-phenylethyl)-2H-imidazol-2-thione

In 100 ml toluene is placed 15 g 1,3-dihydro-4-methyl-5-(2-phenylacetyl)-2H-imidazol-2-thione and 15 g phosphorus pentasulfide. The mixture is refluxed 5 hours and the solvent is evaporated to give the title compound.

Additionally, in a like manner substituting 4-(1-oxobutyl)-1,3-dihydro-5-ethyl-2H-imidazol-2-one, 1,3-dihydro-4-methyl-5-[(3,4-methylenedioxyphenyl)acetyl]-2H-imidazol-2-one or 1,3-dihydro-4-[(1H-pyrrol-2-yl)acetyl]-2H-imidazol-2-one for 1,3-dihydro-4-methyl-5-(2-phenylacetyl)-2H-imidazol-2-thione of the above example yields, respectively, 1,3-dihydro-4-ethyl-5-(1-thioxobutyl)-2H-imidazol-2-one, 1,3-dihydro-4-methyl-5-[2-(3,4-methylenedioxyphenyl)-1-thioxoethyl]-2H-imidazol-2-one and 1,3-dihydro-4-[2-(1H-pyrrol-2-yl)-1-thioxoethyl]-2H-imidazol-2-one.

EXAMPLE 9

| Preparation of a Tablet Formulation | |
|---|---|
| | Per Tablet |
| (a) 1,3-Dihydro-4-methyl-5-(1-oxopropyl)-2H-imidazol-2-one | 100 mg |
| (b) Cornstarch | 15 mg |
| (c) Lactose | 33.5 mg |
| (d) Magnesium stearate | 1.5 mg |

EXAMPLE 10

| Preparation of a Parenteral Formulation | |
|---|---|
| (a) 1,3-Dihydro-4-methyl-5-(2-phenylacetyl)-2H-imidazol-2-one | 1.000 g |
| (b) Polyoxyethylene sorbitan monooleate | 2.000 g |
| (c) Sodium chloride | 0.128 g |
| (d) Water for injection qs ad | 20.000 ml |

We claim:

1. A method for the treatment of cardiac failure in a patent in need thereof which comprises administering to said patient a cardiotonically effective amount of a compound of the formula

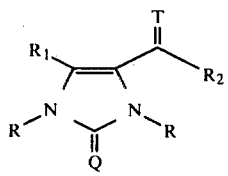

wherein Q and T are each an oxygen atom or a divalent sulfur atom; R is hydrogen, lower alkyl, lower alkanoyl or benzoyl; $R_1$ is hydrogen or lower alkyl; $R_2$ is a saturated straight or branched chain alkyl group of from 2 to 8 carbon atoms, cycloalkyl or cycloalkenyl of from 3 to 7 carbon atoms and cycloalkylalkylene or cycloalkenylalkylene wherein the cycloalkyl or cycloalkenyl moiety has from 3 to 7 carbon atoms; a phenyl alkylene, or furanylalkylene, thienylalkylene, pyridylalkylene, and pyrrylalkylene; and the pharmaceutically acceptable salts thereof.

2. A method of claim 1 wherein R is hydrogen and Q and T are each an oxygen atoms.

3. A method of claim 2 wherein $R_1$ is a methyl group.

4. A method of claim 2 wherein $R_1$ is an ethyl group.

5. A method of claim 2 wherein $R_1$ is a hydrogen atom.

6. A method of claim 2 wherein $R_2$ is ethyl.

7. A method of claim 2 wherein $R_2$ is cyclopropyl.

8. A method of claim 2 wherein $R_2$ is isopropyl.

* * * * *